United States Patent [19]

Croom, Jr. et al.

[11] Patent Number: 5,912,227

[45] Date of Patent: *Jun. 15, 1999

[54] METHOD OF ENHANCING NUTRIENT UPTAKE

[75] Inventors: Warren J. Croom, Jr., Cary, N.C.; Anthony R. Bird, Julia Creek, Australia; Ian Logan Taylor, Johns Island, S.C.

[73] Assignee: North Carolina State University, Raleigh, N.C.

[ * ] Notice: This patent issued on a continued prosecution application filed under 37 CFR 1.53(d), and is subject to the twenty year patent term provisions of 35 U.S.C. 154(a)(2).

[21] Appl. No.: 08/379,354

[22] Filed: Jan. 27, 1995

[51] Int. Cl.$^6$ ............................. A61K 38/16; C07K 14/00
[52] U.S. Cl. ............................................... 514/12; 530/324
[58] Field of Search ................................ 530/324; 514/12

[56] References Cited

U.S. PATENT DOCUMENTS

| 4,701,441 | 10/1987 | Kaira | 514/12 |
| 4,839,343 | 6/1989 | Waeber et al. | 514/12 |
| 5,604,203 | 2/1997 | Balasubramaniam | 514/12 |

FOREIGN PATENT DOCUMENTS

WO 93/24515  12/1993  WIPO .

OTHER PUBLICATIONS

A. Bird et al.; Jejunal Glusose Absorption is Enhanced by Epidermal Growth Factor in Mice, *American Institute of Nutrition* 231–240 (1994).

T. Gaginella; Absorption and secretion in the colon, *Current Science* 5–10 (1994).

A. Bilchick et al.; Peptide YY is a Physiological Regulator of Water and Electrolyte Absorption in the Canine Small Bowel in Vivo, *Gastroenterology* 105:1441–1448 (1993).

L. Pironi et al.; Fat–induced Ileal Brake in Human: A Dos–Dependent Phenomenon Correlated to the Plasma Levels of Peptide YY, *Gastroenterology* 105:733–739 (1993).

T. Zhang et al.; Characterization of Peptide–YY Release in Response to Intracolonic INfusion of Amino Acids, *Endocrinology* 132:553–558 (1993).

K. Opleta–Madsen et al.; Epidermal growth factor upregulates intestinal electrolyte and nutrient transport, *American Physiological Society* (1991).

R. Playford et al.; Preliminary report: role of peptide YY in defence against diarrhoea, *The Lancet* 335:1555–1557 (1990).

C. Yeo et al.; Meal–stimulated absorption of water and electrolytes in canine jejunum, *American Pysiological Society* (1990).

A. Servin et al.; Peptide–YY and Neuropeptide–Y Inhibit Vasoactive Intestinal Peptide–Stimulated Adenosine 3',5'–Monophosphate Production in Rat Small Intestine: Structural Requirements of Peptides for Interacting with Peptide–YY Preferring Receptors, *Endocrinology* 124:692–700 (1989).

M. Schwartz et al.; Influence of Epidermal Growth Factor on Intestinal Funtcion in the Rat: Comparison of Systemic Infusion versus Luminal Perfusion, *American Journal of Surgery* 155:18–22 (1988).

A. Savage et al.; Effects of peptide YY (PYY) on mouth to caecum intestinal transit time and on the rate of gastric empyting in healthy volunteers, *Gut,* 28:166–170 (1987).

T. Adrian et al.; Human Distribution and Release of a Putative New Gut Hormone, Peptide YY, *Gastrenterology,* 89:1707–1077 (1985).

T. Adrian et al.; Effect of Peptide YY on Gastric, Pancreatic, and Biliary Function in Humans, *Gastroenterology,* 89:494–499 (1985).

Morley et al.; Peptide YY(PYY), a Potent Orexigenic Agent, *Brain Research,* 341:200–203 (1985).

Caplus AN. 103: 116740 to Morley et al., Brain Res. 341(1) 200–3 1985.

Welton et al; Role of Na$^+$–Glucose Contransport in Meal–Induced Jejunal Absorption, From the Dept of Surgery, UCLA School of Medicine, 147–148.

A.J. Bilchik et al.; Digestive Disease week and the 94$^{th}$ Annual Meeting of the American Gastroenterological Association, May 15–21, 1993, Boston Massachusetts (AGA Abstract entitled Physiological Significance of Peptide YY (PYY) in Small Intestinal Absorption In Vivo, *J. of Gastroenterology,* Supplement to 104(4):A236 (Apr. 1993).

Friel et al.; Neuropeptide Y: a powerful modulator of epithelial ion transport, *Br. J. Pharmac.,* 88:425–431 (1986).

R. J. MacFadyen et al.; NPY Stimulates Nett Absorption Across Rat Intestinal Mucosa In Vivo, *Neropeptides,* 7:219–227 (1986).

Saria et al.; Neuropeptide Y (NPY) and Peptide YY (PYY) Inhibit Prostaglandin E$_2$ –Induced Intestinal Fluid and Electrolyte Secretion In The Rat Jejunum In Vivo, *European J. of Pharma.,* 119:47–52 (1985).

L.D. Weinstein et al.; Enhanced Intestinal Absorption After, *Arch Surg,* 99:560–562 (Nov. 1969).

Zhang et al, *Endocrinology,* 132, 553–557 (1993).

Bilchik et al, Gastroenterology, 105, 1441–1448, 1993.

Savage et al, Gut, 1987, 28, 166–170.

Playford, et al The Lancet, pp. 1555–1557. 1990.

Yeo, et al, American Physiological Society, G402–G409, 1990.

*Primary Examiner*—Cecilia J. Tsang
*Assistant Examiner*—Bennett Celsa
*Attorney, Agent, or Firm*—Myers Bigel Sibley & Sajovec

[57] ABSTRACT

Methods using Peptide YY (PYY) receptor agonists to increase absorption of nutrients from the intestine without a concomitant increase in intestinal energy expenditure. Methods using Peptide YY (PYY) antagonists to decrease absorption of nutrients from the intestine. Pharmaceutical formulations comprising PYY receptor agonists, such as the PYY peptide and analogs thereof, and pharmaceutical formulation comprising PYY antagonists.

25 Claims, 1 Drawing Sheet

METHOD OF ENHANCING NUTRIENT UPTAKE

FIELD OF THE INVENTION

The present invention relates to methods of increasing nutrient uptake from the intestinal tract in both man and animals, and more specifically relates to increasing the uptake of sodium dependent co-transported nutrients without a concomitant increase in energy expenditure by the intestinal tract.

BACKGROUND OF THE INVENTION

There are no methods commercially available to increase absorption of nutrients from the intestine using exogenous administration of therapeutic agents. There are reports in the literature that epidermal growth factor (EGF) increases the absorption of electrolytes and nutrients such as glucose and proline from the intestine. Opleta-Madsen et al., *Am. J. Physiol.* 260:G807 (1991); M. Schwartz and R. Storozuk, *Am. J. Surgery*, 155:18 (1988)).

Waeber, et al., U.S. Pat. No. 4,839,343, discloses the use of neuropeptide Y (NPY) and peptide Y (PYY) for intravenous administration to a subject to treat hypotension. The peptides are reported to be able to prevent the blood pressure fall induced by certain endotoxins associated with, for example, bacteremia and septic or anaphylactic shock.

WO 93/24515 (Cornell Research Foundation), discloses the identification and cloning of a human NPY/PYY receptor, and discloses the development of antisense oligonucleotides complementary to the receptor mRNA, which oligonucleotides can be used to inhibit the contractile action of neuropeptide Y in human blood vessels.

A. Bilchik et al., *Gastroenterology* 105: 1441 (1993), reports that peripheral infusion of PYY in unfed dogs produced a dose-dependent increase in water and electrolyte absorption from the small intestine. Absorption of fluid and electrolytes from the intestine is known to increase after a meal (meal-induced jejunal absorption); Bilchik et al. report that the infusion of a physiologically effective dose of PYY augmented this proabsorptive response in both the jejunum and ileum.

SUMMARY OF THE INVENTION

A first aspect of the present invention is a method of enhancing gastrointestinal absorption of a sodium dependent co-transported nutrient. The method comprises administering a peptide YY (PYY) receptor agonist to the subject in an amount which enhances the gastrointestinal absorption of the nutrient. The PYY receptor agonist may comprise the PYY peptide.

A further aspect of the present invention is a method of improving the nutritional status of a subject. The method comprises administering a peptide YY (PYY) receptor agonist in an amount which increases the uptake of sodium dependent co-transported nutrients from the intestine. The PYY receptor agonist may comprise the PYY peptide.

A further aspect of the present invention is a method of decreasing the active uptake of glucose in the gastrointestinal tract of a subject. The method comprises administering a peptide YY (PYY) receptor antagonist in an amount which decreases the active gastrointestinal absorption of glucose.

A further aspect of the present invention is a method of increasing the weight gain of a subject. The method comprises administering a peptide YY (PYY) agonist to the subject.

A further aspect of the present invention is a method of treating diarrhea by increasing intestinal water absorption in a subject. The method comprises administering a peptide YY (PYY) receptor agonist in an amount which increases intestinal water absorption.

A further aspect of the present invention is a pharmaceutical formulation comprising, in a physiologically acceptable carrier, an active agent selected from PYY peptide, a PYY receptor agonist or a PYY receptor antagonist.

Further aspects of the present invention include the use of the PYY peptide or a PYY receptor agonist for the manufacture of a medicament for treating conditions where an increase in nutrient, glucose, or water uptake is desirable, and the use of a PYY receptor antagonist for the manufacture of a medicament for treating conditions where a decrease in nutrient, glucose, or water uptake is desirable.

The use of PYY differs from the use of EGF in surprising and unexpected ways, most significantly in the fact that the energetic cost of the transport of nutrient with PYY is significantly lower than with EGF.

DETAILED DESCRIPTION OF THE INVENTION

Figure 1:
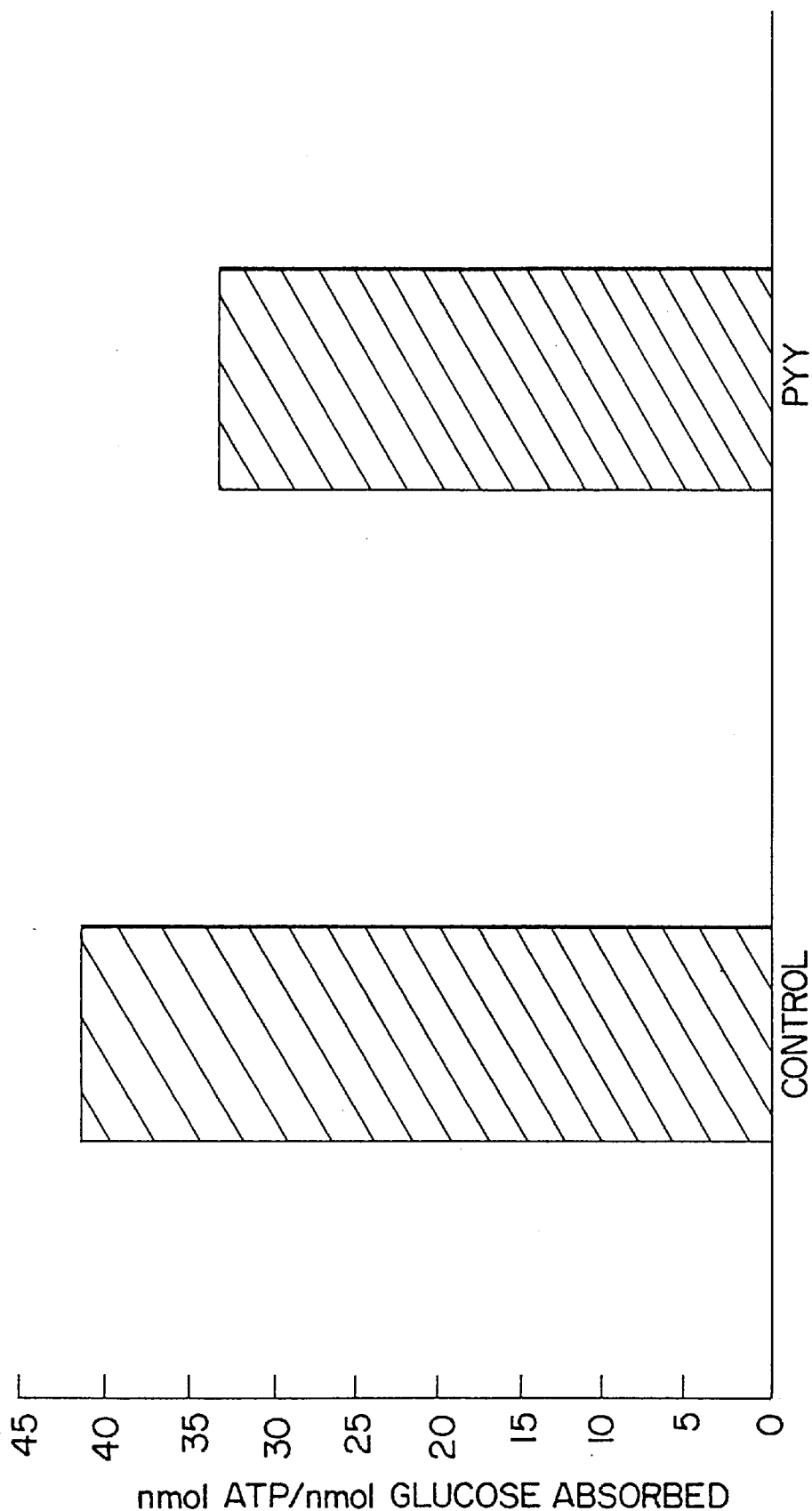
FIG. 1 graphically compares the energy expended in the sodium-dependent active uptake of glucose in mouse intestine, with and without exogenous PYY. Energy expenditure is provided in nanomoles of ATP expended per nanomole of glucose absorbed.

PYY has not previously been described as an enhancer of sodium dependent co-transported nutrient transport within the small intestine. The present inventors have unexpectedly found that exogenously administered PYY not only increases nutrient transport across the intestinal absorptive epithelial cell (enterocyte) luminal membrane, the transport is increased without a concomitant increase in energy expenditure by the intestinal tract. The methods of the present invention have applications in both human and veterinary therapeutics, as well as in animal husbandry and in drug screening techniques.

In the intestine, transport of substances across the absorptive epithelial cell luminal membrane occurs by active transport and by passive transport. Active transport occurs against an electric or chemical gradient, requires the expenditure of energy, is carrier-mediated, and is subject to competitive inhibition. Passive transport occurs with the electric or chemical gradient, does not require energy and is not carrier-mediated. The absorption of both amino acids and sugars occurs by an active transport mechanism and requires the presence of sodium ions. See Hediger and Rhoads, *Molecular Physiology of Sodium-Glucose Cotransporters, Physiological Reviews*, 74:993–1026 (1994). While there are reports in the literature that epidermal growth factor (EGF) increases the absorption of electrolytes and nutrients such as glucose and proline from the intestine (Opleta-Madsen et al., *Am. J. Physiol.* 260:G807 (1991)), it is also reported that the energetic cost of transporting each unit of nutrient is similar to that described for control animals (Bird et al., *J. Nutr.* 124:231 (1994)).

The luminal active glucose transporter in the small intestine, S-GLT1, is a protein whose structure is encoded by one gene of a family of genes that also encode the structure for a sodium-dependent proline transporter and a sodium dependent neutral amino acid transporter (also known as Transporter A). Hence it is probable that agents that increase sodium-dependent intestinal glucose transport will also increase sodium-dependent amino acid transport. This was observed recently in sheep injected with recombinant bovine growth hormone, where sodium-dependent duodenal active transport of glucose increased by approximately 60% and transport of proline increased by approximately 30%. Bird, A. R., *Regulation of Small Intestinal Nutrient Absorption*, Ph.D. Thesis, North Carolina State University, Department of Animal Science, 1994.

As used herein, nutritional status refers to caloric uptake (i.e., absorption from the gut rather than mere ingestion), and enhancing nutritional status refers to increasing total caloric uptake over that which would otherwise occur. As used herein, nutrients refers to both carbohydrates, such as glucose, and amino acids, such as proline. As used herein, an increase (or decrease) in active uptake of a nutrient due to treatment of a subject with a PYY receptor agonist or antagonist refers to increased (or decreased) nutrient uptake over that which would have occurred in the subject without PYY treatment. Similarly, an increase or decrease in water absorption, and an increase or decrease in weight gain, refers to an increase or decrease over that which would have occurred in the subject without PYY treatment. As used herein, enhancing gastrointestinal absorption of a nutrient refers to either (1) increasing the absorption of a nutrient without a concomitant increase in energy expenditure, or (2) to decreasing the energy expenditure required to absorb a given amount of nutrient (each as compared to nutrient absorption in the subject without any treatment). As used herein growth and growth enhancement refer to increases in either, or both, weight and height over that which would otherwise occur.

1. Description of PYY

PYY (peptide tyrosine tyrosine) is a 36 amino acid hormonal peptide, produced by "L type" endocrine cells. See Boucher et al., *Regul. Pept.* 13:283 (1986). PYY is a member of the pancreatic polypeptide family, which includes pancreatic polypeptide (PP) and neuropeptide Y (NPY) in addition to Peptide YY. PPY is released in response to feeding and has a variety of effects on the gastrointestinal tract, including inhibition of gastric acid secretion, inhibition of pancreatic exocrine secretion, delay of gastric emptying, and slowing of intestinal transit (see Savage et al., *Gut*, 28, 166 (1987); Pironi et al., *Gastroenterology* 105, 733 (1993); Adrian et al. *Gastroenterology* 89:494 (1985).

Binding studies using labelled PYY have demonstrated the presence of a PYY receptor in rat small intestine. Servin et al., *Endocrinology*, 124, 692 (1989), used fragments of PYY peptide to study the structural requirements of peptides for competing with labelled PYY for binding to intestinal membranes, and reported that fragments of PYY acted as agonists of intact PYY, although at reduced biological activity.

In addition to the PYY peptide, PYY receptor agonists and antagonists may also be used in the methods of the present invention. As used herein "PYY agonist" means a substance which binds to the PYY receptor and induces the same physiologic responses as PYY. As used herein, "PYY antagonist" means a substance which binds to the PYY receptor and blocks the physiologic effect of PYY.

2. Uses of PYY in Methods of the Present Invention

The PYY peptide and PYY agonists used in the methods of the present invention increase feed utilization efficiency in domestic livestock by increasing nutrient uptake without a concomitant increase in intestinal energy expenditure, thereby increasing the production efficiency of animal products such as meat, wool and milk, while decreasing the amount of animal fecal waste. As used herein, domestic livestock or domesticated livestock refers to animal species commonly raised in captivity and selectively bred for desirable characteristics, including but not limited to rate of growth, conformation, or meat, fur, egg or milk production. Domestic livestock include bovines, ovines, porcines, caprines, equines, avians, lagomorphs, felines and canines.

Recent studies indicate that in strains of domestic livestock highly selected for their rapid growth, the intestine's ability to absorb nutrients may be a growth limiting factor. In other words, the intestine functions at or near its assimilation limit so that increasing nutrient ingestion will not result in an increase in nutrient assimilation, and will not therefor contribute to increased growth. Croom et al., *J. Dairy Science*, 76:2112–2124 (1993). Recent work by Obst and Diamond indicate that in strains of domestic chickens, the intestinal capacity to absorb nutrients imposes limits on normal growth. Obst and Diamond, *Auk* 109, 451–464 (1992). Thus in addition to therapeutic uses, methods of the present invention may be used in normal (healthy) domestic animals to increase feed utilization efficiency, and thus increase growth above that which could be achieved by any increase in feed intake alone.

PYY or PYY agonists may also be used to increase nutrient uptake for therapeutic reasons in both humans and animals. Therapeutic uses include, but are not limited to, increasing the rate of growth, the rate of weight gain, and the survival rate of premature offspring, neonates, and the aged; increasing total nutrient uptake in subjects with short bowel syndrome or with surgical resection of the intestine; and improving nutritional status of subjects with eating disorders such as anorexia nervosa and bulimia, subjects with acquired immune deficiency syndrome or other chronic immune deficiency syndromes, individuals with Down's syndrome, and burn victims or other severely traumatized subjects.

The PYY peptide and its receptor agonists may also be used in methods of the present invention for treating diarrheal diseases, including cholera. An important function of the sodium dependent glucose cotransporters is to increase fluid absorption from the gut. Hediger and Rhoads, *Physiol. Reviews*, 74: 993–1026 (1994). Current treatments for cholera include the infusion of glucose to increase the absorption of water from the intestine; water and sodium are co-transported across the intestinal mucosa along with glucose. Use of PYY or its receptor agonists in the methods of the present invention will increase glucose transport, resulting in the increased co-transport of water and sodium without a concomitant increase in energy expenditure by the intestinal tract.

PYY receptor antagonists may be used where a reduction in the uptake of nutrients, and in particular the uptake of glucose, is desired. This may occur, for example, in hyperglycemic conditions, diabetes, and chronic obesity.

The PYY peptide, its receptor agonists and antagonists may also be used to screen substances for PYY receptor ligand activity, as binding to the receptor is subject to competitive inhibition. Methods of screening substances, such as by competitive binding assays, are known in the art and would be apparent to one skilled in the art.

In the manufacture of a medicament according to the present invention, hereinafter referred to as a pharmaceutical formulation, the active compound (PYY, PYY agonist or PYY antagonist, or analogs thereof) is typically admixed with a pharmaceutically acceptable carrier. The carrier may be either solid or liquid, such as sterile, pyrogen-free water or sterile pyrogen-free phosphate-buffered saline solution. The carrier is preferably formulated with the active compound as a unit-dose formulation, for example, a tablet which may contain from 0.5% to 95% by weight of the active compound. One or more active compounds may be incorporated in the formulations of the invention, which may be prepared by any of the well known techniques of pharmacy.

As the PYY peptide, its agonists and antagonists described above are the active ingredient in the formulations, they are included in an amount effective to accomplish the intended treatment. In general, PYY or its agonists are administered to a subject to be treated in an effective nutrient transport stimulating amount; PYY antagonists are included in an effective nutrient transport inhibiting amount. The precise amount to be administered to the subject is determined in a routine manner, and will vary depending on the subject, the condition being treated and the condition of the subject, and the route of administration. In general, for PYY the dosage administered will be sufficient to result in peak plasma PYY concentrations of from about $1\times10^{-1}$, $1\times10^{0}$ or $1\times10^{1}$ picomole per Liter to about $1\times10^{2}$, $1\times10^{3}$ or even $1\times10^{4}$ picomole per Liter or more. Preferred dosages may be determined by simply administering a composition containing a known amount of active ingredient to a subject, and monitoring the subject for the desired effect, as would be known by one skilled in the art.

For the preparation of these compositions, use can be made of pharmaceutical carriers adapted for conventional forms of administration, for example, injection solutions, tablets, capsules, dragees, syrups, solutions, suspension and the like. As an injection medium, it is preferred to use water which contains the additives usual in the case of injection solutions, such as stabilizing agents, salts or saline, and/or buffers. The active agent or its pharmaceutical formulation may be contained within a nutritional medium, e.g., in infant formulas or nutritional supplements. Oral formulations may be slow release preparations or enteric coated preparations to facilitate delivery of the peptide to the small intestine.

Any suitable route of administration may be employed in carrying out the methods of the present invention, including administration by parenteral injection (e.g., subcutaneous, intravenous, intramuscular, or intradermal), and oral, nasal, rectal, or topical administration.

Subjects to be treated by the methods disclosed herein include those of any species, but are preferably mammalian or avian subjects. The term "avian" as used herein is intended to encompass all avian species, including but not limited to, chickens, turkeys, ducks, geese, quail, and pheasant. Mammalian subjects include, but are not limited to, human, bovine, ovine, porcine, caprine, equine, lagomorph, feline and canine subjects. Thus the present invention has both human medical and veterinary medical applications, as well as applications in livestock industries.

The peptides of the present invention may be made in accordance with techniques known in the art. Using accepted techniques of chemical synthesis, the peptide is built up either from the N-terminus or, more typically, the C-terminus using either single amino acids or preformed peptides containing two or more amino acid residues.

3. Analogs

Analogs of the PYY peptide are an aspect of the present invention. As used herein, an "analog" is a chemical compound similar in structure to a first compound, and having either a similar or opposite physiologic action as the first compound. With particular reference to the present invention, PYY peptide analogs are those compounds which, while not having the amino acid sequences of the PYY peptide, are capable of binding to the PYY receptor. Such analogs may be peptide or non-peptide analogs, including nucleic acid analogs, as described in further detail below.

In protein molecules which interact with a receptor, the interaction between the protein and the receptor must take place at surface-accessible sites in a stable three-dimensional molecule. By arranging the critical binding site residues in an appropriate conformation, peptides which mimic the essential surface features of the PYY peptide may be designed and synthesized in accordance with known techniques. International PCT Application WO 93/24515 (Cornell Research Foundation, Inc.) reports the cloning and identification of a human NPY/PYY receptor.

Methods for determining peptide three-dimensional structure and analogs thereto are known, and are sometimes referred to as "rational drug design techniques". See, e.g., U.S. Pat. No. 4,833,092 to Geysen; U.S. Pat. No. 4,859,765 to Nestor; U.S. Pat. No. 4,853,871 to Pantoliano; U.S. Pat. No. 4,863,857 to Blalock; (applicants specifically intend that the disclosures of all U.S. Patent references cited herein be incorporated by reference herein in their entirety). See also Waldrop, *Science*, 247, 28029 (1990); Rossmann, *Nature*, 333, 392–393 (1988); Weis et al., *Nature*, 333, 426–431 (1988); James et al., *Science*, 260, 1937 (1993) (development of benzodiazepine peptidomimetic compounds based on the structure and function of tetrapeptide ligands).

In general, those skilled in the art will appreciate that minor deletions or substitutions may be made to the amino acid sequences of peptides of the present invention without unduly adversely affecting the activity thereof. Thus, peptides containing such deletions or substitutions are a further aspect of the present invention. In peptides containing substitutions or replacements of amino acids, one or more amino acids of a peptide sequence may be replaced by one or more other amino acids wherein such replacement does not affect the function of that sequence. Such changes can be guided by known similarities between amino acids in physical features such as charge density, hydrophobicity/hydrophilicity, size and configuration, so that amino acids are substituted with other amino acids having essentially the same functional properties. For example: Ala may be replaced with Val or Ser; Val may be replaced with Ala, Leu, Met, or Ile, preferably Ala or Leu; Leu may be replaced with Ala, Val or Ile, preferably Val or Ile; Gly may be replaced with Pro or Cys, preferably Pro; Pro may be replaced with Gly, Cys, Ser, or Met, preferably Gly, Cys, or Ser; Cys may be replaced with Gly, Pro, Ser, or Met, preferably Pro or Met; Met may be replaced with Pro or Cys, preferably Cys; His may be replaced with Phe or Gln, preferably Phe; Phe may be replaced with His, Tyr, or Trp, preferably His or Tyr; Tyr may be replaced with His, Phe or Trp, preferably Phe or Trp; Trp may be replaced with Phe or Tyr, preferably Tyr; Asn may be replaced with Gln or Ser, preferably Gln; Gln may be replaced with His, Lys, Glu, Asn, or Ser, preferably Asn or Ser; Ser may be replaced with Gln, Thr, Pro, Cys or Ala; Thr may be replaced with Gln or Ser, preferably Ser; Lys may be replaced with Gln or Arg; Arg may be replaced with Lys, Asp or Glu, preferably Lys or Asp; Asp may be replaced with Lys, Arg, or Glu, preferably Arg or Glu; and Glu maybe replaced with Arg or Asp, preferably Asp. Once made, changes can be routinely screened to determine their effects on function with enzymes.

Non-peptide mimetics of the peptides of the present invention are also an aspect of this invention. Non-protein drug design may be carried out using computer graphic modeling to design non-peptide, organic molecules able to bind to the PYY receptor. See, e.g., Knight, *BIO/Technology*, 8, 105 (1990). Itzstein et al, *Nature*, 363, 418 (1993) (peptidomimetic inhibitors of influenza virus enzyme, sialidase). Itzstein et al modeled the crystal structure of the sialidase receptor protein using data from x-ray crystallography studies and developed an inhibitor that would attach to active sites of the model; the use of nuclear magnetic resonance (NMR) data for modeling is also known in the art. See also Lam et al, *Science*, 263, 380 (Jan. 1994) regarding the rational design of bioavailable nonpeptide cyclic ureas that function as HIV protease inhibitors. Lam et al used information from x-ray crystal structure studies of HIV protease inhibitor complexes to design nonpeptide inhibitors.

Analogs may also be developed by generating a library of molecules, selecting for those molecules which act as ligands for a specified target, and identifying and amplifying the selected ligands. See, e.g., Kohl et al., *Science*, 260, 1934 (1993) (synthesis and screening of tetrapeptides for inhibitors of farnesyl protein transferase, to inhibit ras oncoprotein dependent cell transformation). Techniques for constructing and screening combinatorial libraries of oligomeric biomolecules to identify those that specifically bind to a given receptor protein are known. Suitable oligomers include peptides, oligonucleotides, carbohydrates, nonoligonucleotides (e.g., phosphorothioate oligonucleotides; see *Chem. and Engineering News*, page 20, 7 Feb. 1994) and nonpeptide polymers (see, e.g., "peptoids" of Simon et al., *Proc. Natl. Acad. Sci. USA*, 89, 9367 (1992) ) . See also U.S. Pat. No. 5,270,170 to Schatz; Scott and Smith, *Science*, 249, 386–390 (1990); Devlin et al., *Science* 249, 404–406 (1990); Edgington, *BIO/Technology*, 11, 285 (1993). Peptide libraries may be synthesized on solid supports, or expressed on the surface of bacteriophage viruses (phage display libraries). Known screening methods may be used by those skilled in the art to screen combinatorial libraries to identify PYY receptor ligands. Techniques are known in the art for screening synthesized molecules to select those with the desired activity, and for labelling the members of the library so that selected active molecules may be identified. See, e.g., Brenner and Lerner, *Proc. Natl. Acad. Sci. USA*, 89, 5381 (1992) (use of genetic tag to label molecules in a combinatorial library); PCT US93/06948 to Berger et al., (use of recombinant cell transformed with viral transactivating element to screen for potential antiviral molecules able to inhibit initiation of viral transcription); Simon et al., *Proc. Natl. Acad. Sci. USA*, 89, 9367, (1992) (generation and screening of "peptoids", oligomeric N-substituted glycines, to identify ligands for biological receptors); U.S. Pat. No. 5,283,173 to Fields et al., (use of genetically altered *Saccharomyces cerevisiae* to screen peptides for interactions).

As used herein, "combinatorial library" refers to collections of diverse oligomeric biomolecules of differing sequence, which can be screened simultaneously for activity as a ligand for a particular target. Combinatorial libraries may also be referred to as "shape libraries", i.e., a population of randomized polymers which are potential ligands. The shape of a molecule refers to those features of a molecule that govern its interactions with other molecules, including Van der Waals, hydrophobic, electrostatic and dynamic.

Nucleic acid molecules may also act as ligands for receptor proteins. See, e.g., Edgington, *BIO/Technology*, 11, 285 (1993). U.S. Pat. No. 5,270,163 to Gold and Tuerk describes a method for identifying nucleic acid ligands for a given target molecule by selecting from a library of RNA molecules with randomized sequences those molecules that bind specifically to the target molecule. A method for the in vitro selection of RNA molecules immunologically cross-reactive with a specific peptide is disclosed in Tsai, Kenan and Keene, *Proc. Natl. Acad. Sci. USA*, 89, 8864 (1992) and Tsai and Keene, *J. Immunology*, 150, 1137 (1993). In the method, an antiserum raised against a peptide is used to select RNA molecules from a library of RNA molecules; selected RNA molecules and the peptide compete for antibody binding, indicating that the RNA epitope functions as a specific inhibitor of the antibody-antigen interaction.

C. Peptides, Agonists and Antagonists

The term PYY peptide agonist as used herein refers to molecules that bind to PYY receptors and result in the increased uptake of glucose without a concomitant increase in intestinal energy expenditure. PYY agonists may be fusion proteins containing the PYY peptide sequence or may be formed by modifying the PYY peptide's natural amino acid sequence or modifying the N-terminal amino and/or the C-terminal carboxyl group, and include salts formed with acids and/or bases, particularly physiologically acceptable inorganic and organic acids and bases. Preferred modifications are those which provide a more stable, active peptide which will be less prone to enzymatic degradation in vivo.

Peptides of the present invention may be made in accordance with techniques known in the art. Using accepted techniques of chemical synthesis, the peptide is built up either from the N-terminus or, more typically, the C-terminus using either single amino acids or preformed peptides containing two or more amino acid residues. Particular techniques for synthesizing peptides include (a) classical methods in which peptides of increasing size are isolated before each amino acid or preformed peptide addition, and (b) solid phase peptide synthesis in which the peptide is built up attached to a resin such as a Merrifield resin. In these synthetic procedures, groups on the amino acids will generally be in protected form using standard protecting groups such as t-butoxycarbonyl. If necessary, these protecting groups are cleaved once the synthesis is complete. Other modifications may be introduced during or after the synthesis of the peptide. Peptides of the present invention may also be produced through recombinant DNA procedures as are known in the art.

The following examples are provided to illustrate the present invention, and should not be construed as limiting thereof. In these examples, g means gram, mg means milligram, µg means microgram, cc means cubic centimeter, mm means millimeter, µmol means micromole, pmol means picomole, nmol means nanomole, min means minute, µL means microLiter, 3OMD means tritiated 3-O-Methyl-D-glucose, and phlorizin means phloretin-2'-β-D-glucoside.

EXAMPLE 1

Materials and Methods

Two month old male swiss-webster mice obtained from Charles River Laboratory were subcutaneously injected in the post-scapula region once a day for three days with one of the following treatments: (1) Saline treatment: 0.25 ml of sterile physiological saline (0.9% saline) (n=9 mice); (2) Peptide YY (PYY) treatment: 300 µg per kilogram body weight of Peptide YY in 0.25 ml sterile physiological saline solution (n=6 mice); (c) Somatostatin treatment: 120 µg per kilogram body weight of somatostatin in 0.25 ml sterile physiological saline solution (n=6 mice); or (4) Transforming Growth Factor alpha (TGFα) treatment: 300 μg per kilogram body weight of TGFα in 0.25 ml sterile physiological saline solution (n=6 mice).

TGFα was chosen as a comparative treatment because the TGFα peptide is homologous to EGF and has similar biological effects, and binds to the EGF receptor (Todaro et al., *Proc. Natl Acad. Sci. USA* 77:5258 (1980)). Somatostatin was chosen as a comparative treatment because a role for somatostatin in intestinal absorption of nutrients has been suggested by some researchers.

EXAMPLE 2

Food Intake, Empty Body Weight and Small Intestinal Weight and Length in Treated Mice During the three days of the injection protocol describe in Example 1, mice were allowed free access to a commercial pelleted rodent chow (ground prior to feeding) and food intake was measured in grams of feed consumed per mouse over the three day period. After the final injection the mice were fasted for eighteen hours and then sacrificed by cervical dislocation. Body weight was measured after the three days' fast (Fasting Body Weight) and prior to sacrifice by cervical dislocation. After sacrifice, the small intestine was removed and the weight and length were measured.

Results are shown in Table 1. No significant differences were found among the four treatment groups in food intake, fasting body weight, and length of small intestine. The small intestine weight was significantly greater in the somatostatin treatment group (P<0.05) for reasons which are unclear. Small intestine weight in the somatostatin group may have increased due to hypertrophy or hyperplasia of the intestine. In comparing the results for the saline, PYY and TGFα groups, no significant differences were seen in weight and length of small intestine, indicating that any increase in nutrient transport in these groups is due to an increase in the activity of the transport process rather than an increase in the number of absorptive cells (enterocytes).

EXAMPLE 3

Effect of Systemic Administration of Select Peptides on Jejunal Glucose Transport A sample of mid-jejunal tissue was dissected out of each of the small intestines removed in Example 2. As described below, each glucose transport assay was replicated three times per mouse, and an assay to measure non-specific binding was replicated twice per mouse. Thus each mid-jejunal sample (one from each mouse) was cut into eight one millimeter rings.

The assay for glucose transport was a modification of the assay validated by Black, *Comp. Biochem Physiol.* 90A:379 (1988) to measure glucose transport in embryonic chick duodenum. Additional details of the present method as modified for mouse intestine are discussed in Bird et al., *J. Nutr.* 124:231 (1994), and the method is validated for mice in Bird et al., *Nutr. Research*, 14:411 (1974). The transport buffer utilized for jejunal samples was similar to that described by Black (1988) but also contained 0.5 mmol/L 3-O-methyl-D-glucose (3 OMG), 0.5 mmol/L B-hydroxybutyrate, and 2.5 mmol/L glutamine. The assay was started by transferring intestinal rings preincubated at 37° C. for 5 minutes in transport buffer to beakers containing 28 MBq/L of [$^3$H]3 OMG in 2 ml of buffer. To differentiate active from passive transport, phlorizin (phloretin-2'-β-D-glucoside; Sigma Chemicals, St. Louis, Mo.) was utilized. Phlorizin is a specific inhibitor of the S-GLT1 transporter (a sodium dependent active transporter) located on the luminal surface of absorptive epithelium (see Brot-Laroche and Alvarado, Mechanisms of sugar transport across the intestinal brush border membrane, IN: *Intestinal Transport: Fundamental and Comparative Aspects*, Gilles-Baillin and Gilles (Eds.), Springer-Verlag, Berlin (1983)). The S-GLT1 transporter is one of a family of transporter proteins, and actively transports glucose. 3 OMD is transported by S-GLT1, but is not metabolized by the epithelial cell and hence accumulates in the cell (see Kimmich and Randalls, *J. Membrane Biol.* 23:57 (1975). Phlorizin was added at 1 mmol/L to the buffer in an additional set of incubations. A 5 minute concomitant incubation of duplicate samples at 4° C. measured nonspecific binding of [$^3$H]3 OMG. Thus each mid-jejunal sample was cut into eight one millimeter rings; three rings were assayed in the absence of phlorizin at 37° C., three rings were assayed in the presence of phlorizin at 37° C., and two rings were assayed in the presence of phlorizin at 4° C. to measure background nonspecific binding of [$^3$H]3 OMG.

Uptake of [$^3$H]3 OMG was stopped after 5 minutes by rinsing samples in 3 ml of ice-cold mannitol (300 mmol/L). Labelled substrate was extracted from the tissue into 2 mL of trichloroacetic acid (25 g/L) at 37° C. for 60 minutes in a shaking water bath. Samples were removed, blotted and weighed. The extract was centrifuged at 2000×g for 15 minutes at 4° C., and then 1 ml of the decanted supernatant was dispersed in 5 ml of Ecolite (+) scintillation cocktail (ICN Biomedicals, Cleveland, Ohio) and counted for 10 minutes in a scintillation counter. Duplicate aliquots (100 uL) of incubation media containing approximately 2.8 kBq [$^3$H]3 OMG (both with and without phlorizin) and a blank were counted with each set of samples.

Active glucose transport was calculated as the difference between 3 OMG accumulation in media with and without phlorizin. Passive transport was calculated as the difference between 3 OMG accumulation in the presence of phlorizin at 37° C. and 4° C. Total transport is the difference between 3 OMG accumulation at 37° C., in the absence of phlorizin, and accumulation at 4° C. in the presence of phlorizin. Transport data are presented as pmol glucose/(min-mg wet tissue). Fasting body weight of the mice was used to express data on a body weight basis.

As shown in Table 2, PYY administration resulted in a statistically significant increase (P=0.5) in active glucose transport (provided in picomoles of glucose transported per minute per milligram of intestinal tissue) compared to transport in the saline control group. When glucose transport was expressed per unit of fasting body weight (calculations not shown), a 46% increase in active glucose transport was seen in the PYY treatment group compared to the saline control group; this increase in glucose transport attributable to the PYY treatment is statistically significant (P=0.03).

EXAMPLE 4

Effect of Peptide Treatments on Visceral Organ Weight

After the treated mice were sacrificed by cervical dislocation as described in Example 2, the visceral organs were dissected out and the liver, stomach, kidneys, colon and caecum of each mouse was weighed. Results are provided in Table 3. The kidneys of the PYY treatment group were heavier than those of other treatment groups for unknown reasons. When organ weight was standardized to fasting body weight, no significant differences in organ weight were seen among the treatment groups; the kidneys of the PYY treatment group were not statistically heavier than those of other groups (P=0.09).

EXAMPLE 5

Effect of Peptide Treatments on Jejunal Oxygen Consumption in Mice

Measurement of oxygen consumption rate was determined as described by McBride and Milligan, Br. *J. Nutr.*, 53:605 (1985) for ovine duodenal mucosa, and as described by Bird et al., *J. Nutr.* 124:231 (1994) for mice jejunum, using an oxygen monitor and an incubation bath fitted with an $O_2$ electrode (Yellow Springs Instruments, Yellow Springs, Ohio, USA). Adjacent jejunal ring samples (two from each mouse jejunum) were prepared by rinsing in ice-cold HEPES transport buffer to remove digesta residues. The rate of $O_2$ uptake of the duplicate jejunal samples, constantly stirred in 4 ml of media at 37° C., was electronically recorded. After 3 minutes, 100 uL of 12.6 mmol/L ouabain (Sigma Chemical), a specific inhibitor of Na+, K+-ATPase, was added to the chamber and oxygen consumption was plotted for 3 minutes. Dry matter content of the tissue pieces was then measured by drying the jejunal samples at 80° C. in a forced draught oven for 48 hours.

Results are shown in Table 4. No significant differences in oxygen consumption were found among the treatment groups (P>0.05).

EXAMPLE 6

Energetic Efficiency of Na-Dependent Active Glucose Uptake

The energetic efficiency of Na-dependent active glucose uptake in the PYY treated mice and the saline control treated mice was calculated, assuming that consumption of 1 nmol of $O_2$ (as measured in Example 5, above) indicated expenditure of 5 nmol of ATP (Gill et al., *J. Nutr.* 119:1287–1299 (1989).

Comparing the total nmol ATP expended per nmol of 3OMG uptake between the saline control treatment and the PYY treatment, as shown in FIG. 1, indicates that the metabolic cost of total glucose uptake from the intestinal lumen is less in the PYY treatment group (reduced nmol ATP/nmol glucose uptake in PYY treatment group).

The foregoing examples are illustrative of the present invention, and are not to be construed as limiting thereof. The invention is defined by the following claims, with equivalents of the claims to be included therein.

TABLE 1

Food Intake, Fasting Body Weight, Small Intestinal Weight and Length in Mice Treated with Select Peptides

| Treatment (N) | Food Intake (g) | Fasting Body Weight (g) | Weight Small Intestine (g) | Length Small Intestine (mm) |
|---|---|---|---|---|
| Saline Control (9) | 10.3 | 28.4 | 1.810 | 450 |
| PYY (6) | 9.2 | 27.5 | 1.652 | 454 |
| Somatostatin (6) | 9.1 | 27.7 | 2.127* | 467 |

TABLE 1-continued

Food Intake, Fasting Body Weight, Small Intestinal Weight and Length in Mice Treated with Select Peptides

| Treatment (N) | Food Intake (g) | Fasting Body Weight (g) | Weight Small Intestine (g) | Length Small Intestine (mm) |
|---|---|---|---|---|
| TGFα (6) | 11.0 | 28.8 | 1.999 | 461 |
| SEM[1] | 2.3 | 1.1 | 0.244 | 25 |

[1]Pooled SEM (Standard Error of the Mean)
*Comparisons with other treatment groups are significantly different, P < 0.05

TABLE 2

Effect of Systemic Administration of Peptides on Jejunal Glucose Transport

| | Glucose Transport (pmol/min/mg tissue) | | |
|---|---|---|---|
| Treatment (N) | Active | Passive | Total |
| Saline Control (9) | 264 | 81 | 345 |
| PYY (6) | 369[2,3] | 63 | 431 |
| Somatostatin (6) | 303 | 67 | 371 |
| TGFα (6) | 347 | 64 | 410 |
| SEM[1] | 88 | 48 | 102 |

[1]Pooled SEM
[2]Significance of PYY effects for active glucose transport: P = 0.05 compared to control treatment
[3]When glucose transport was expressed per unit of body weight, a 46% increase in active glucose transport was attributable to PYY treatment (compared to saline control); this increase was statistically significant (P = 0.31).

TABLE 3

Effect of Peptide Treatment on Visceral Organ Weight

| Treatment | Organ Weight (mg) | | | | |
|---|---|---|---|---|---|
| (N) | Liver | Stomach | Kidneys | Colon | Caecum |
| Control (9) | 1417 | 239 | 511 | 324 | 149 |
| PYY (6) | 1274 | 230 | 468[2,3] | 315 | 134 |
| Somatost.(6) | 1441 | 232 | 534 | 316 | 156 |
| TGFα (6) | 1442 | 243 | 522 | 379 | 156 |
| SEM[1] | 141 | 22 | 30 | 67 | 27 |

[1]Pooled SEM
[2]Significantly different compared to control (P < 0.05)
[3]No significant differences when organ weight normalised to fasted body weight (effects of PYY treatment on kidney weight, P = 0.09).

TABLE 4

Effect of Select Peptides on Jejunal Oxygen Consumption in Mice

| | Oxygen Consumption ($\mu$L/min/g)[1] | | | |
|---|---|---|---|---|
| Treatment (N) | Without Ouabain Wet | Without Ouabain Dry | With Ouabain Wet | With Ouabain Dry |
| Control (9) | 45.74 | 242.83 | 35.73 | 190.40 |
| PYY (6) | 47.71 | 253.93 | 36.54 | 194.22 |
| Somatostatin (6) | 43.62 | 224.77 | 35.13 | 181.29 |
| TGF$\alpha$ (6) | 47.96 | 238.76 | 36.03 | 179.01 |
| SEM[2] | 8.95 | 39.84 | 6.98 | 33.13 |

[1]Oxygen consumption of wet and dry jejunum in the presence and absence of ouabain.
[2]Pooled SEM with 21 degrees of freedom.
No significant (P > 0.05) treatment differences.

We claim:

1. A method of increasing the weight gain of a healthy subject, comprising administering peptide YY (PYY) to said subject in an amount effective to increase weight gain of said subject by enhancing gastrointestinal absorption of a sodium-dependent cotransported nutrient, wherein said administration is carried out by a method selected from the group consisting of parenteral, oral, nasal, rectal, and topical routes of administration.

2. A method according to claim 1, wherein said subject is selected from the group consisting of bovine, ovine, porcine, caprine, equine, avian, lagomorph, feline and canine subjects.

3. A method according to claim 1, wherein said subject is a human subject.

4. A method according to claim 1, wherein the PYY administration further improves the efficiency of feed utilization by said subject.

5. A method of increasing the weight gain of a healthy domestic livestock animal selected from the group consisting of bovines, ovines, porcines, caprines, equines, avians and lagomorphs, comprising administering peptide YY (PYY) to said animal in an amount effective to increase weight gain of said animal by enhancing gastrointestinal absorption of a sodium-dependent cotransported nutrient, wherein said administration is carried out by a method selected from the group consisting of parenteral, oral, nasal, rectal, and topical routes of administration.

6. A method according to claim 5, wherein said animal is a high-producing domestic livestock animal.

7. A method according to claim 5, wherein said animal is a high-producing domestic livestock animal in which gastrointestinal nutrient absorption is rate-limiting for production.

8. A method according to claim 5, wherein said animal has been selected from a rapid-growth strain.

9. A method according to claim 5, wherein said animal is a growing domestic livestock animal in which gastrointestinal nutrient absorption is rate-limiting for growth.

10. A method according to claim 5, wherein said animal is being raised for meat production, wool production, milk production, fur production, or egg production.

11. A method according to claim 5, wherein said animal is selected from the group consisting of bovines, ovines, porcines, caprines, equines, and lagomorphs.

12. A method according to claim 5, wherein the PYY administration further improves the efficiency of feed utilization by said animal.

13. A method of increasing the weight gain of a healthy domesticated avian, comprising administering peptide YY (PYY) to said domesticated avian in an amount effective to increase weight gain of said domesticated avian by enhancing gastrointestinal absorption of a sodium-dependent cotransported nutrient, wherein said administration is carried out by a method selected from the group consisting of parenteral, oral, nasal, rectal, and topical routes of administration.

14. A method according to claim 13, wherein said domesticated avian is a high-producing domesticated avian.

15. A method according to claim 13, wherein said domesticated avian is a high-producing domesticated avian in which gastrointestinal nutrient absorption is rate-limiting for production.

16. A method according to claim 13, wherein said domesticated avian has been selected from a rapid-growth strain.

17. A method according to claim 13, wherein said domesticated avian is a growing domesticated avian in which gastrointestinal nutrient absorption is rate-limiting for growth.

18. A method according to claim 13, wherein said domesticated avian is being raised for meat production or egg production.

19. A method according to claim 13, wherein said domesticated avian is selected from the group consisting of chickens, turkeys, ducks, geese, quail and pheasant.

20. A method according to claim 13, wherein said domesticated avian is a turkey.

21. A method according to claim 13, wherein said domesticated avian is a chicken.

22. A method according to claim 13, wherein the PYY administration further improves the efficiency of feed utilization by said domesticated avian.

23. A method according to any one of claims 1, 5 or 13, wherein said sodium dependent co-transported nutrient is glucose.

24. A method according to any one of claims 1, 5 or 13, wherein said sodium dependent co-transported nutrient is an amino acid.

25. A method according to any one of claims 1, 5 or 13, wherein said sodium dependent co-transported nutrient is proline.

* * * * *